(12) United States Patent
Zei et al.

(10) Patent No.: US 8,303,172 B2
(45) Date of Patent: Nov. 6, 2012

(54) DEVICES AND METHODS FOR EXERCISE MONITORING

(76) Inventors: Paul Zei, Burlingame, CA (US); Bryant Lin, Menlo Park, CA (US); Robert C. Allison, Rancho Palos Verdes, CA (US); Kenneth Carr, Woolwich, ME (US)

( * ) Notice: Subject to any disclaimer, the term of this patent is extended or adjusted under 35 U.S.C. 154(b) by 0 days.

(21) Appl. No.: 12/969,834

(22) Filed: Dec. 16, 2010

(65) Prior Publication Data

US 2011/0176578 A1 Jul. 21, 2011

Related U.S. Application Data

(63) Continuation of application No. PCT/US2009/047519, filed on Jun. 16, 2009.

(60) Provisional application No. 61/132,335, filed on Jun. 16, 2008.

(51) Int. Cl.
*G01J 5/10* (2006.01)
*A61B 5/01* (2006.01)

(52) U.S. Cl. ........ 374/122; 374/120; 374/163; 600/407; 600/549; 600/474; 702/131

(58) Field of Classification Search .................. 374/120, 374/122, 163, 183, 141, 100; 340/870.17, 340/573.1; 600/474, 549, 407, 300; 702/131
See application file for complete search history.

(56) References Cited

U.S. PATENT DOCUMENTS

| | | | | |
|---|---|---|---|---|
| 4,129,125 A * | 12/1978 | Lester et al. | ................... | 600/484 |
| 4,138,998 A * | 2/1979 | Nowogrodzki | ............... | 600/430 |
| 4,235,107 A * | 11/1980 | Ludeke et al. | ................ | 374/122 |
| 4,312,358 A | 1/1982 | Barney | | |
| 4,479,498 A * | 10/1984 | Toftness | ........................ | 600/407 |
| 4,488,559 A * | 12/1984 | Iskander | ........................ | 600/430 |
| 4,774,961 A * | 10/1988 | Carr | ............................... | 600/549 |
| 4,926,868 A * | 5/1990 | Larsen | .......................... | 600/407 |
| 5,176,146 A * | 1/1993 | Chive et al. | ................... | 600/549 |
| 5,284,144 A * | 2/1994 | Delannoy et al. | ............. | 600/412 |
| 5,664,578 A | 9/1997 | Boczan | | |
| 5,688,050 A * | 11/1997 | Sterzer et al. | ................. | 374/122 |
| 5,841,288 A * | 11/1998 | Meaney et al. | ................ | 324/639 |
| 5,949,845 A * | 9/1999 | Sterzer | ............................ | 378/37 |
| 5,983,124 A * | 11/1999 | Carr | ............................... | 600/407 |
| 6,543,933 B2 * | 4/2003 | Stergiopoulos et al. | ....... | 374/122 |
| 7,197,356 B2 * | 3/2007 | Carr | ............................... | 600/430 |
| 8,013,745 B2 * | 9/2011 | Icove et al. | ................. | 340/573.1 |
| 2003/0045804 A1 * | 3/2003 | Brodnick | ....................... | 600/509 |
| 2005/0101872 A1 * | 5/2005 | Sattler et al. | .................. | 600/483 |
| 2005/0276309 A1 * | 12/2005 | Koch | ............................ | 374/208 |

(Continued)

FOREIGN PATENT DOCUMENTS

DE 10005526 A1 * 8/2001

(Continued)

OTHER PUBLICATIONS

International Search Report for WO2010/005727 completed on Jan. 20, 2010.

*Primary Examiner* — Gail Verbitsky

(74) *Attorney, Agent, or Firm* — Goodwin Procter LLP

(57) ABSTRACT

The disclosure relates to methods and devices for monitoring e.g., fatigue levels by measuring a subject's body core temperature. In one embodiment, microwave radiometry is used to measure such core temperature.

4 Claims, 8 Drawing Sheets

U.S. PATENT DOCUMENTS

| | | |
|---|---|---|
| 2007/0270282 A1 | 11/2007 | Falcone |
| 2007/0299488 A1* | 12/2007 | Carr .............................. 607/101 |
| 2010/0160809 A1* | 6/2010 | Laurence et al. ............. 600/549 |
| 2011/0028799 A1* | 2/2011 | Hyde et al. .................... 600/300 |
| 2011/0245653 A1* | 10/2011 | Varahramyan et al. ....... 600/407 |
| 2011/0263969 A1* | 10/2011 | Fontius ......................... 600/412 |
| 2012/0029359 A1* | 2/2012 | Sterzer et al. ................. 600/474 |
| 2012/0053445 A1* | 3/2012 | Turnquist et al. ............. 600/407 |

FOREIGN PATENT DOCUMENTS

| | | | |
|---|---|---|---|
| SU | 1287004 A | * | 1/1987 |
| WO | WO-2006/131908 A2 | | 12/2006 |

* cited by examiner

Accessory Radiometer Sensor (Side View)

DEVICES AND METHODS FOR EXERCISE MONITORING

RELATED APPLICATION

This application is a continuation of PCT/US2009/047519, filed Jun. 16, 2009, which claims priority to provisional application U.S. Ser. No. 61/132,335, filed Jun. 16, 2008 hereby incorporated by reference in its entirety.

BACKGROUND

Athletes have long sought ways to improve their performance through a variety of often complex training regimens. Optimizing training and competition by avoiding fatigue and not significantly exceeding anaerobic threshold is extremely important to improve performance.

Physiologic monitoring can be used to assess whether athletes are reaching their fatigue and anaerobic threshold (i.e. exceeding their exercise capacity). The most common monitoring metric is heart rate. When athletes approach or reach a predetermined target heart rate or heart rate range (zone), they can modify their exertion level (e.g. pace) to avoid fatiguing too soon. A variety of portable devices including watches with wireless heart rate sensors are being used to measure heart rate during exercise. However, heart rate is an imperfect metric and has significant variability due to influence from endogenous and exogenous factors.

Another method of measuring or evaluating fatigue in a subject may be temperature. Fatigue may occur at, for example, repeatable, predictable core body and muscle temperature thresholds. However, skin temperature is significantly less effective at predicting fatigue due to influence from the ambient temperature and other factors.

Previous studies evaluating core and muscle temperature during exercise utilized invasive measurements of temperature such as rectal, invasive muscle probes and/or oral methods. These standard methods of measuring core and muscle temperature are cumbersome and most people would not utilize them during exercise. Similarly, while microwave radiometry has been utilized in temperature measurement including measuring temperature from specific locations from a satellite, such microwave radiometry devices are typically large and not portable. For example, radiometers have been disclosed in e.g., U.S. Pat. Nos. 4,346,716, 4,647,281, 4,774,961, 5,334,141, 5,662,110, 5,779,635; and 5,983,124, hereby incorporated by reference.

Currently, there appears to be no system or device that permits non-invasive, comfortable assessment of core body or muscle temperature during exercise. Further, there is an on-going need, especially for athletes, for devices and methods of assessing or monitoring e.g. fatigue during exercise.

SUMMARY

The present disclosure generally provides methods and devices for monitoring core temperature of the body, e.g. during exercise.

Disclosed herein, in part, is a wearable radiometer for continuously or periodically measuring core body, muscle and other internal organ temperatures, for example, during exercise. Also disclosed herein are methods, systems and devices for the continuous or periodic measurement of core body, muscle or other internal organ temperature during exercise that may include exertional feedback which may, for example, prevent and evaluate fatigue, anaerobic threshold and/or exercise capacity.

For example, provided herein is a non-invasive method of assessing fatigue and/or anaerobic threshold in a subject during physical exertion, comprising measuring core body or muscle temperature of said subject, for example, wherein the measuring core body temperature comprises the using microwave radiometry. Such measuring core body temperature may include providing a wearable device to said subject during physical exertion. Such device may, in some embodiments, provide a sensory signal (e.g. visual, tactile, or audio) detectable by said subject when a predetermined core body or muscle temperature is reached.

In another embodiment, provided herein is a method of controlling a subject's physical activity comprising monitoring the subject's core body or muscle temperature. Such methods may further comprise adjusting said physical activity once a selected core body or muscle temperature is achieved. Such monitoring may include providing a device that comprises a microwave radiometer and a transducer for detecting core body or muscle microwave emissions and positioning said device on said subject at a position suitable for detecting the subject's core body or muscle temperature substantially continuously during physical exertion, an audio, visual or tactile signal, where the signal configured for indicating when the subject's core body or muscle temperature is at a selected level, for example, a predetermined temperature, or a predetermined change in temperature over a set time. Disclosed methods may include providing a display unit configured for displaying the subject's core body or muscle temperature, for example positioned so that the temperature displayed by said display unit can be viewed by a subject, e.g. the subject wearing a wearable radiometer device.

Contemplated physical activity may include walking, running, swimming, bicycling, skating, skiing, climbing, wheelchairing, snowshoeing, or the like.

Also provided herein is a wearable apparatus for measuring core body temperature during exercise, comprising: an antenna; a microwave radiometer circuit; a microcontroller; and a power supply; all or some of which may be disposed within a device body suitable for continuous use on a subject during exercise. For example, the device body may be suitable for use on a subject's extremities, or is suitable for use as an earpiece, suitable for use on the body, or is suitable for inserting or attaching to an article of clothing or a shoe. Exemplary device bodies may be suitable for use on a subject's wrist, ankle, finger, hand, toe, arm, leg, chest, torso, head or neck.

For example, disclosed herein is a wearable apparatus for measuring core body temperature or sub-dermal tissue temperature of a subject during exercise, comprising a temperature acquisition unit comprising: an antenna; a microwave radiometer circuit; a low frequency electronics unit; and a power supply, said temperature acquisition unit disposed within a device body configured for continuous use on the subject during exercise. In some embodiments, the wearable apparatus or temperature acquisition unit may further comprise a microcontroller.

In some embodiments, a disclosed wearable apparatus includes an antenna which may be less or equal about 50 mm in the antenna's greatest dimension, e.g. about 2 mm to about 50 mm in diameter, or about 4 mm in length and about 2 mm in diameter, and/or wherein the power supply is a battery.

Disclosed wearable apparatus may further comprise a display unit configured for displaying real time body core temperature data or tissue temperature provided by the microwave radiometer, for example, a display unit may be configured to be worn by the subject so as to be visible to the subject while performing exercise.

In some embodiments, the wearable apparatus or the display unit may further comprise an alarm which is activated when the body core temperature or tissue temperature meets a predetermined target. A disclosed apparatus, e.g. a display unit and/or a temperature acquisition unit, may further comprise at least one memory and at least one processor for processing acquired temperature data in accordance with instructions stored in the at least one memory. Disclosed display units may be configured for communication with a temperature acquisition unit via a wired or wireless link. In some embodiments, a display unit forms part of the temperature acquisition unit. In another embodiment, a display unit is disposed in a separate unit.

Provided herein, in a different embodiment, is a method of substantially continuously self-monitoring core body temperature in a subject, for example, a subject who is exercising, comprising: providing a first wearable device to said subject, wherein said first wearable device comprises a transducer for detecting body core microwave emissions of the subject and a wireless transmission module; providing a second wearable device suitable for self-monitoring to said subject, wherein said second wearable device comprises a transducer, a wireless transmission module, a microwave radiometer integrated circuit chip, and a display user interface for providing the core body temperature information to said subject; detecting body core microwave emissions from the subject using the first wearable device; transmitting said microwave emissions from the first wearable device to the second wearable device; and displaying the core body temperature. A first wearable device may include, for example, a chest strap, and a second wearable device may include an article for attaching to a wrist, arm finger, leg, toe or foot of the subject.

In another embodiment, a method of substantially continuously self-monitoring core body temperature in a subject, e.g. a subject who is exercising, comprising: providing a first wearable device to said subject, wherein said first wearable device comprises a transducer for detecting body core microwave emissions of the subject, a microwave radiometer integrated circuit chip and a wireless transmission module; providing a second wearable device suitable for self-monitoring to said subject, wherein said second wearable device comprises a wireless transmission module and a display user interface for providing the core body temperature information to said subject; detecting body core microwave emissions from the subject and converting the emissions to temperature information using the first wearable device; transmitting said temperature information from the first wearable device to the second wearable device; and displaying the core body temperature using the second wearable device.

Also provided herein is a kit for substantially continuously measuring body core temperature comprising: a first wearable device comprising an antenna, a microwave radiometer circuit, a microcontroller and a power supply; and optionally instructions for use.

DETAILED DESCRIPTION

This disclosure is generally directed to wearable apparatus or device for measuring core body temperature or tissue (e.g. muscle) temperature (for example sub-surface (e.g., below skin)) temperature) in a subject (e.g. in a human) during e.g., exercise, and non-invasive methods for assessing fatigue and/or anaerobic threshold in a subject, e.g., while exercising. Disclosed devices may measure core body or tissue temperatures that fluctuate, for example, due to a subject's regulation of temperature during exercise.

Provided herein, in an embodiment, is a wearable device that includes a radiometer. A radiometer device generally includes four major components: 1) antenna and optional shielding, 2) measurement and calibration apparatus (software and/or hardware), 3) data display and/or communications module and 4) power supply. Disclosed wearable devices are significantly smaller than typical radiometers. For example, disclosed devices include an antenna for localized temperature measurements of the body which may be for example, smaller than or equal to about 4 mm length and 2 mm diameter, or e.g. about 2 mm to about 50 mm in the antenna's greatest dimension. A disclosed antenna may be for example flexible (e.g. a printed antenna) or substantially rigid. For example, an antenna for use in a disclosed device may be proportional to the measurement depth of e.g. tissue. Such antennas may be capable of use in a local volumetric measurement of core body temperature.

Figure 1:
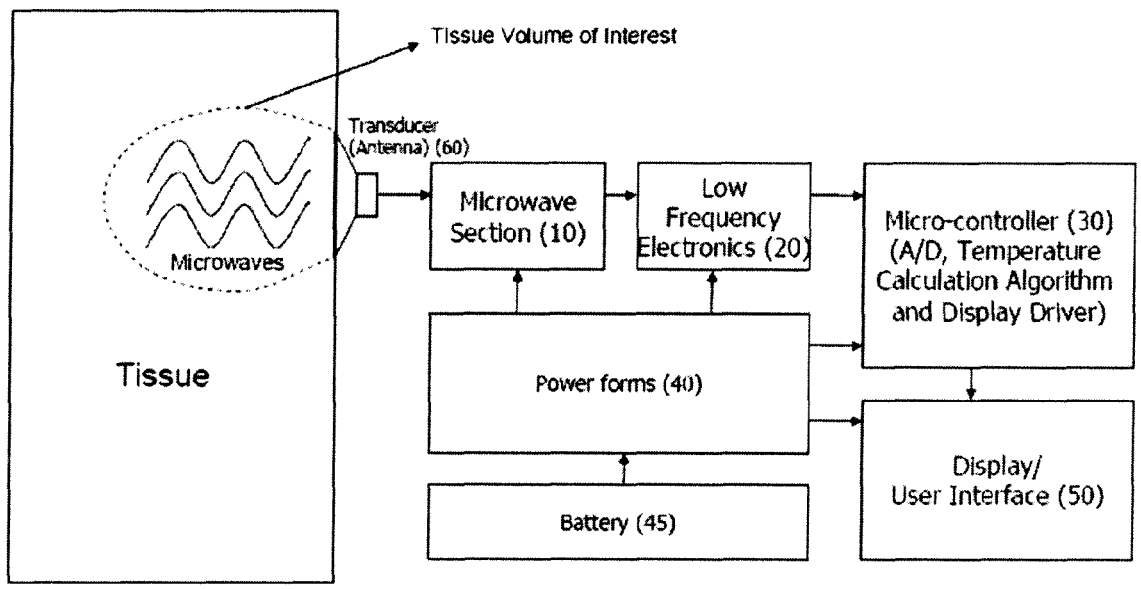
FIG. 1 is a system block diagram showing an apparatus for measuring core body temperature.
Figure 2:
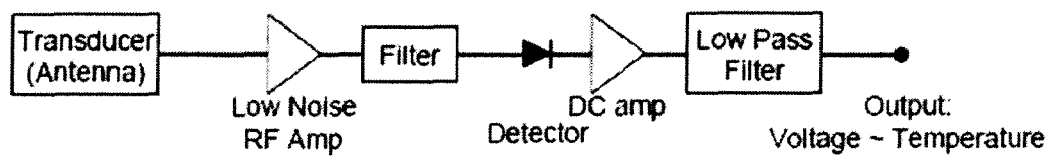
FIG. 2 depicts a microwave radiometry circuit.

Referring to FIG. 1, a disclosed radiometer device may include a transducer or antenna 60 that detects and/or receives microwaves emitted by sub-surface tissue over a specific volume of tissue of interest (e.g. an area of subject's body near core organs, e.g. near the chest). Microwave electronics 10 convert detected microwave signal from the subject into a lower frequency electronic signal that can be filtered, biased and/or otherwise transformed by low frequency electronics 20. The low frequency electronics feed either analog or digital data from which temperature can be calculated to the microcontroller 30. Microwave section 10 may include or form part of a microwave radiometer circuit such as shown in FIG. 2, and as known in the art. A calibration apparatus or microcontroller 30 may include one or more integrated circuits, and/or may include a means for A/D, temperature calculation algorithm and/or a display driver.

The microcontroller 30 can execute algorithmic and/or other operations on the temperature data and/or may display information via a user interface 50. Power forms 40 may include a power supply such as a battery 45, (which may be for example a standard watch, AAA, AA or larger battery (e.g., lithium, nickel-cadmium, and/or alkaline battery). The data display and communication module 50 can be driven by the measurement/calibration apparatus 30 or be self contained, and may display and/or transmit the temperature data.

Microwave section 10 may include, for example, the section (or parts of the section) depicted as a block diagram in FIG. 2. For example, as depicted in FIG. 2, the transducer/antenna can pick up microwave energy and can be tuned to a specific wavelength or range of wavelengths (e.g. at about 1

Ghz to about 4 Ghz). The signal can be amplified by a low noise radio frequency (RF)/microwave amplifier, as shown in FIG. 2, which can feed into a filter to e.g. substantially eliminate noise. Peak or other like detectors may be used to detect an envelope of signal, and the envelope may then be amplified by a DC amplifier and low pass filter as in FIG. 2. The output voltage is proportional to temperature.

Figure 4:
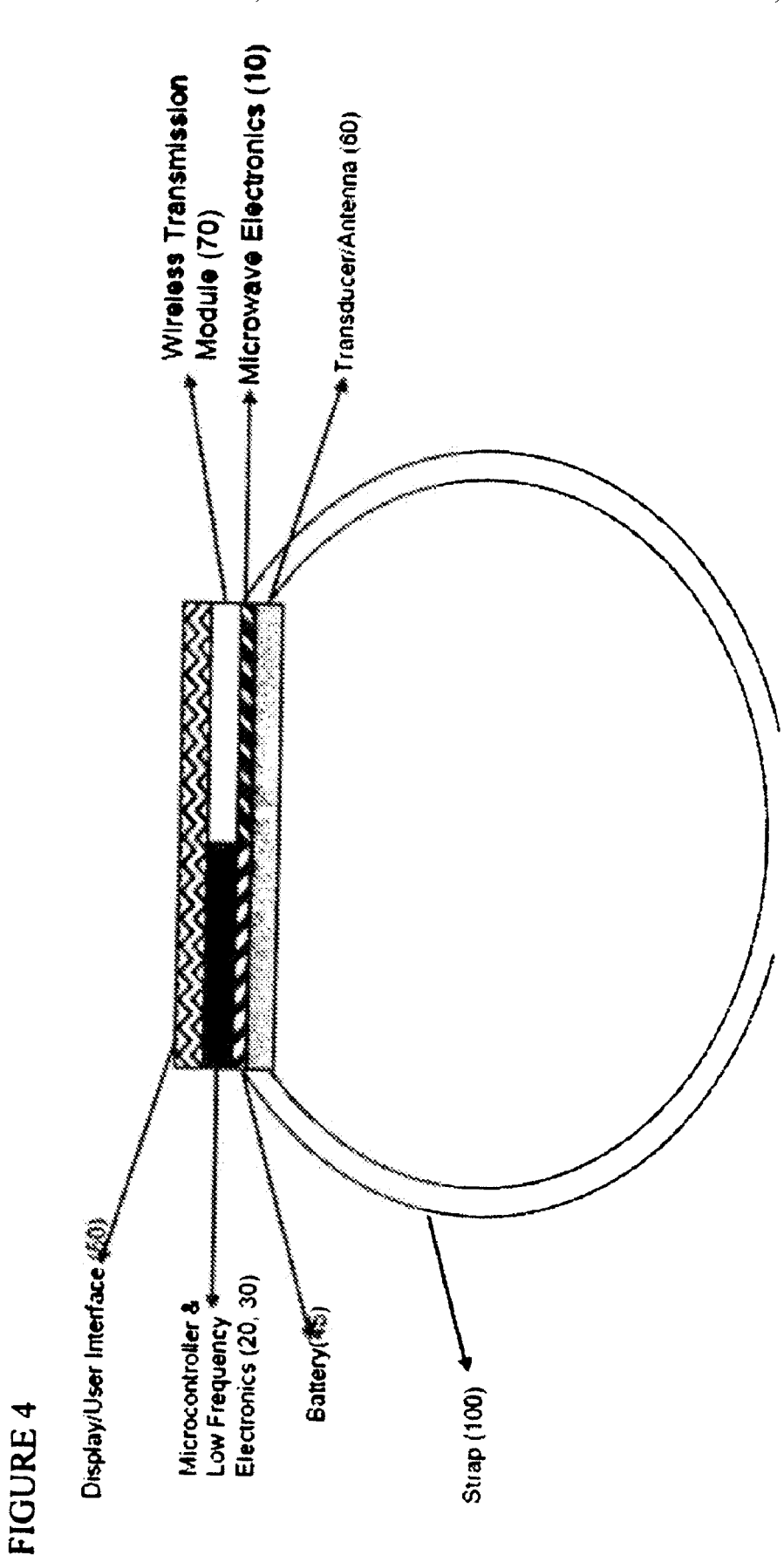
FIG. 4 is a side view of a microwave radiometry device including a strap suitable for use on a subject.

For example, in one embodiment, a disclosed wearable radiometer is a wearable device similar to a wristwatch, for example, as shown in FIG. 4. The body of the wristwatch may contain shielding to decrease noise interference to the antenna. Such a wearable radiometer may include a means for attaching to a subject's body, such as strap 100. While the antenna 60 may be disposed be anywhere in the "watch," in some embodiments, the antenna is positioned next to the skin directed toward e.g. the muscles of an appendage, e.g. the arm of a subject. A power supply 45, measurement/calibration, and/or display/communications 50 may be disposed in the body of the "watch." Typically, any display module is disposed on the side of the watch away from the body for ease of use. Such a display module and "watch" may also capable of measuring and displaying current core body temperature, historic core body temperature measurements, and/or e.g., a temperature graph among other like data. Such a wearable radiometer device may also have the means to function as a digital watch and other devices with functions including but not limited to time, alarm, stopwatch, GPS/mileage, pedometer, oximeter, air temperature, and timer. Other sensors such as for heart rate detection may also be incorporated into the portable radiometer. For example, contemplated herein in one embodiment is an integrated device that provides for velocity, pace, and/or distance traveled information, e.g. gathered by an electronic positioning module, as well as temperature data.

Figure 5:
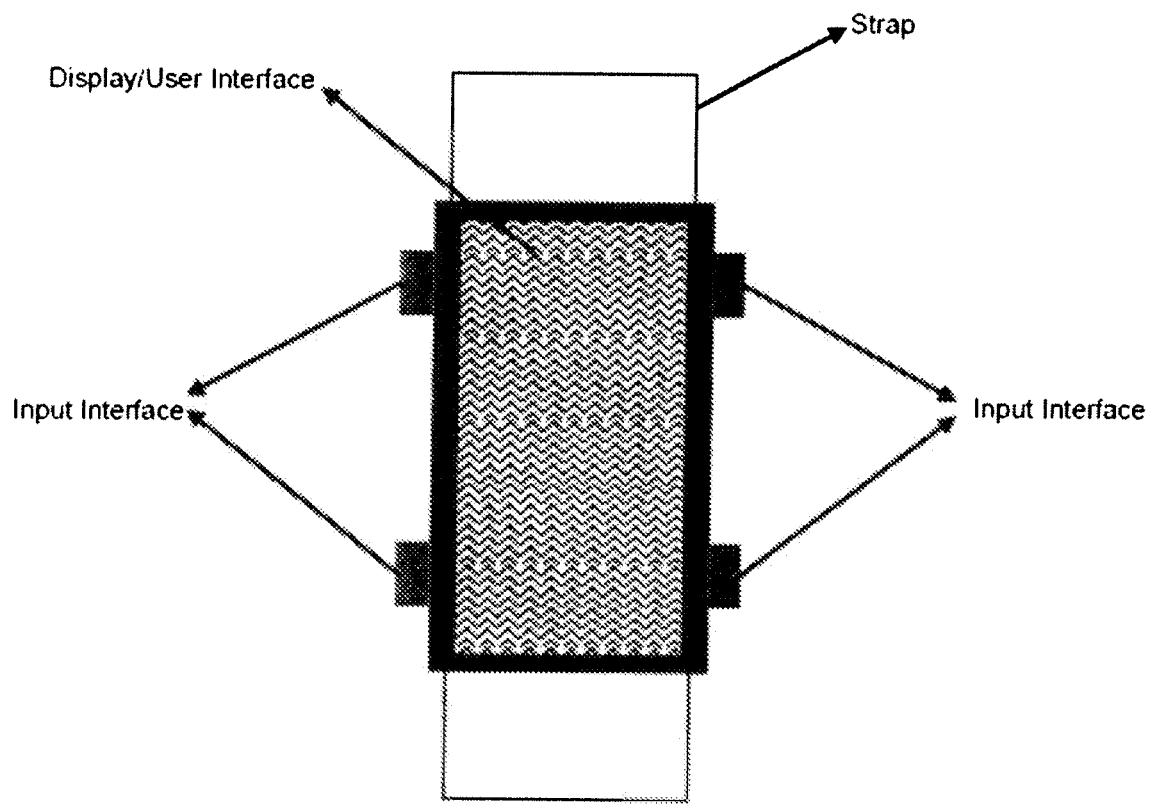
FIG. 5 is a top view of the device of FIG. 4.

For example, a display interface/communications may receive temperature or other data from a microcontroller via a wired or wireless link. A subject may select the type of data to be displayed or may select one or more predetermined formats for data display using input switches which may be disposed on the side of a device, e.g. as in FIG. 5. In an exemplary embodiment, the display component may be programmed such that an alarm would be activated if a data value (e.g. temperature) departs from a predetermined limit or range.

Other embodiments other than a "wristwatch" include incorporating part or all of the radiometer in jewelry, clothing, adhesive patches, shoes, glasses, headphone, music players and headbands.

In some embodiments, a disclosed device such as that depicted in FIG. 4 may transmit or receive data via wireless transmission module 70, which may include an antenna different that that the antenna 60. Such transmission module may use wireless protocols as know to those skilled in the art such as WIFI IEEE 802.11a-g, Bluetooth 1, 2, 3; FM encoding (analog), AM encoding (analog) and/or IEEE 802.15.4 (Zigbee). For example, wireless transmission module 70 may receive temperature information from another device disposed on the subject's body, and/or may transmit information to a computer.

Figure 3:
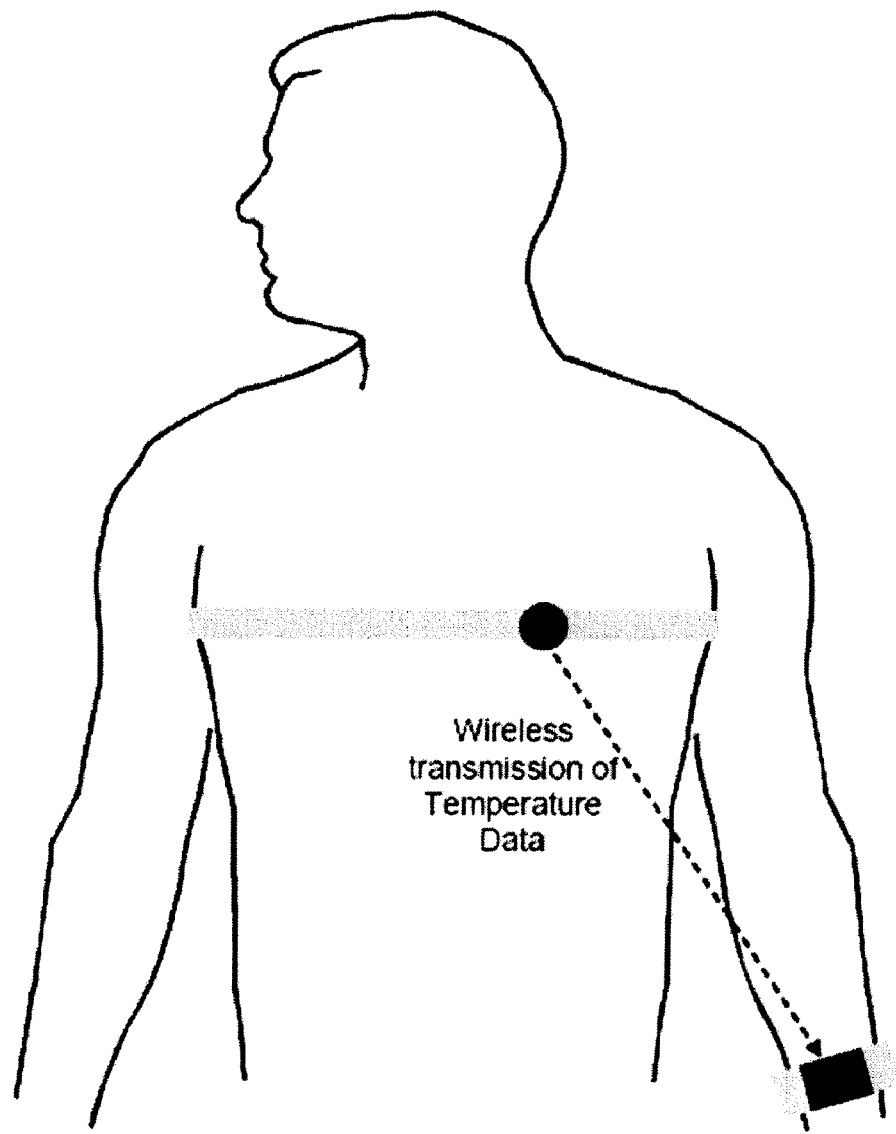
FIG. 3 depicts a wearable chest strap on a subject for detecting core body temperature and the wireless transmission of temperature information to a wrist strap.

A disclosed device such as depicted in FIG. 4 may, in some embodiments, not include microwave electronics 10, low frequency electronics 20, and/or microcontroller 30. For example, microwave electronics 10, low frequency electronics 20, and/or microcontroller 30 may instead, or additionally, be disposed on a second device disposed on the subject's body, e.g. as depicted in FIG. 3

Figure 6:
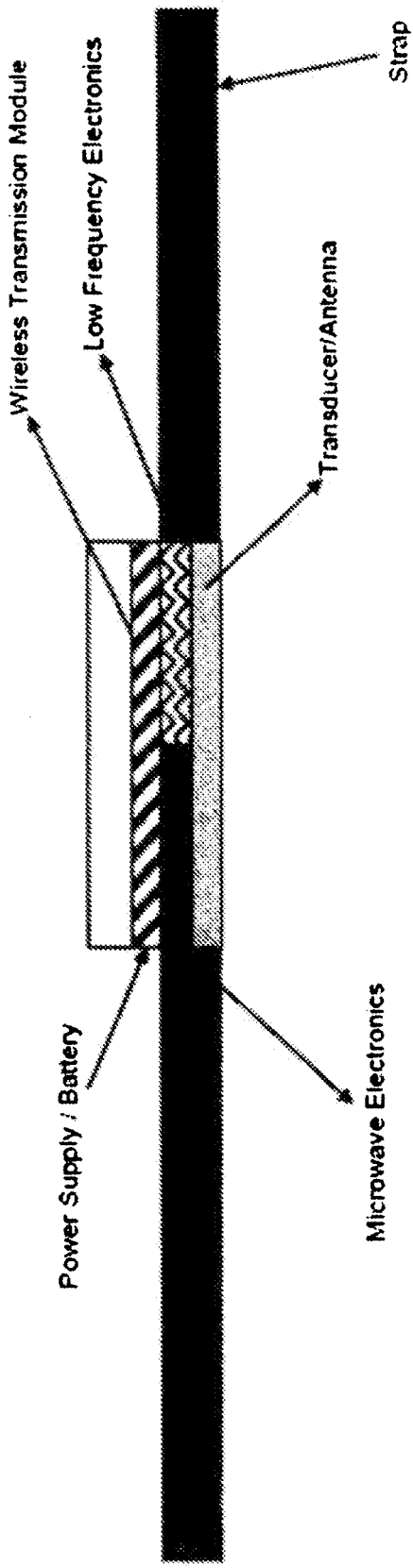
FIG. 6 is a side view of an accessory radiometer sensor device for measuring body core temperature and transmitting to another device.

For example, the display/communications module can also transmit or receive data to or from one or more other devices such as depicted in FIG. 6. FIG. 6 depicts an accessory radiometer that may be placed in a different portion of the body (e.g. chest) for different and/or more efficient or accurate measurement of body core temperature. Such accessory device may transmit temperature information to a device disposed on the subject for e.g. easy viewing, or such device may a stand alone device that in some embodiments may transmit data to a computer for viewing by the subject or third person or may display information for viewing by e.g., a third person such as a trainer or physician.

For example, provided herein is a kit or method that includes both a wearable radiometer suitable for use, e.g. on the chest (or other radiometer sensor), and e.g. a wearable radiometer suitable for use on the wrist, and including a temperature display means. In another embodiment, provided herein is a radiometer device that includes a means for transmitting core body temperature information to computer (e.g. via a wired or wireless connection.)

In an embodiment, disclosed devices may include a primary wearable radiometer and one or more further wearable radiometers and/or other sensors (such as a heart rate sensor, pulse oximetry, blood pressure, pedometry, and/or galvanic response sensors). For example, a primary radiometer receives data from the other radiometers and sensors and displays and/or stores the data. The wearable radiometers may transmit temperature information and may be worn or attached on a muscle or near organs of interest on a subject user. Other sensors such as a heart rate monitor can be strapped to the chest or other locations. Disclosed radiometers and sensors could be used to cross-validate the data coming from any sensor or filter noise by methods such as adaptive filtering.

In an embodiment, disclosed devices include means for one or more alarms, (e.g. an audio (e.g., tone or beep), visual (e.g. flashing light), tactile signal (vibration) to alarm or otherwise alert the user when he or she has entered specified temperature range. Separate alarms/alerts can be programmed, for example, to incorporate temperatures from one or more radiometers or other data such as heart rate. Alarms can be designed separately for each data stream or alarms can be programmed to incorporate multiple data points (e.g. alarm when heart rate>120 beats per minute and temperature from right thigh>40 degrees Celsius). Such alarms or alerts may be activated when temperature data provided by the radiometer meets or does not meet a predetermined target temperature. In another embodiment, an alarm or alert may be activated when the subject's speed, blood oxygen level, or heart rate exceeds or falls short of a predetermined target.

Another embodiment allows for the radiometer or external module (such as a computer) to provide feedback to the user to increase or decrease their exertion stay in a range of temperature. The system and device could provide feedback as a function of one or more radiometers and other sensors. For example, a runner using the system could program in a target comfortable training core body temperature zone specified over the entire training session or as a function of time. If the zone is 39 to 40 degrees Celsius, the radiometer could provide pacing feedback in the form of audible, visual or tactile cues for the user to increase or decrease his or her pace to stay in the zone. The cue could be a beep for every step, for example. If the user's temperature exceeds 40 degrees the beeping frequency would slow. If the user's temperature dropped below 39 degrees, the beeping frequency would increase. The cues could be visual (e.g. flashing light) or tactile (e.g. mechanical pulsing in the wrist band) as well. In another embodiment, distance data such as pedometer data may be utilized as a variable in programming the pacing output cues as later in a training session the user may require a much lower pace to stay in the target temperature zone.

Methods

In an embodiment, this disclosure provides for non-invasive method of assessing fatigue and/or anaerobic threshold in a subject during physical exertion, comprising measuring core body or muscle temperature of said subject, for example, by measuring core body temperature comprises the using microwave radiometry. For example, such a method can include having a subject wear a disclosed wearable device during physical exertion, such as for example, walking, running, swimming, bicycling, skating, skiing, climbing, wheelchairing, or snowshoeing, and/or the like.

As discussed, a disclosed device may provide a sensory signal such as a visual, tactile, or audio detectable signal to the subject when a predetermined core body or muscle temperature is reached.

Also provided herein is a method of controlling a subject's physical activity comprising monitoring the subject's core body or muscle temperature. Such methods may further include adjusting said physical activity once a selected core body or muscle temperature is achieved. Such selected temperature may be provided (e.g. as instructions), otherwise predetermined, or may be based on historical data (e.g. such as obtained in a previous physical activity by the same or different subject). In another embodiment, such monitoring of core body temperature may include direct monitoring of temperature, or may include monitoring of the change in temperature over a set time (e.g. a temperature velocity, $\Delta T/dt$). For example, such monitoring may include providing a device that comprises a microwave radiometer and a transducer for detecting core body or muscle microwave emissions and positioning said device on said subject at a position suitable for detecting the subject's core body or muscle temperature substantially continuously during physical exertion.

Such methods may include providing a display unit configured for displaying the subject's core body or muscle temperature. For example, when a subject is a human, a display unit may be positioned so that the temperature displayed by said display unit can be viewed by said subject.

In some embodiments, disclosed methods and devices may provide for substantially continuous monitoring of body core temperature. Such continuous monitoring refers to discrete intervals which may be closely spaced, e.g. temperature measurements using radiometry at less than or about 0.1, 1 sec, 1 min, 5 min or more intervals, e.g. while a subject is continuously wearing a disclosed device.

EXAMPLES

The examples that follow are intended in no way to limit the scope of this disclosure but are provided to illustrate the methods present disclosure. Many other embodiments of this disclosure will be apparent to one skilled in the art.

Example 1

This study was designed to compare use of a radiometer device during exercise with measurement of body temperature by mouth (PO).

Four runners (SV1, MS1, RV1, RV2) were asked to run on a treadmill at a rate at which they would fatigue after 30 minutes but to keep running until fatigue. After 30 minutes of constant speed running, the runners were asked to cool down slowly at a comfortable pace. PO temperatures were taken using a Vick's Flex Tip thermometer that was tested against a warm water bath at 40 degrees Celsius. The runners had to place the thermometer in their mouths under their tongues while running. A reader records the radiometer temperature and PO temperature.

The microwave radiometer was calibrated against fixed temperature water baths at 30 and 40° C. A radiometer antenna was affixed to the chest of the subjects using a large neoprene strap just underneath the left nipple. A cord connected the antenna to the electronics and the data logging PC.

Runners ran for 25, 35, 35 and 30 minutes each (average 31.3+/−2.4). Peak radiometer temperatures were achieved at an average of 32+/−5.8 minutes. Peak rise in temperature above baseline was 2.8+/−0.7° C.

Figure 7:
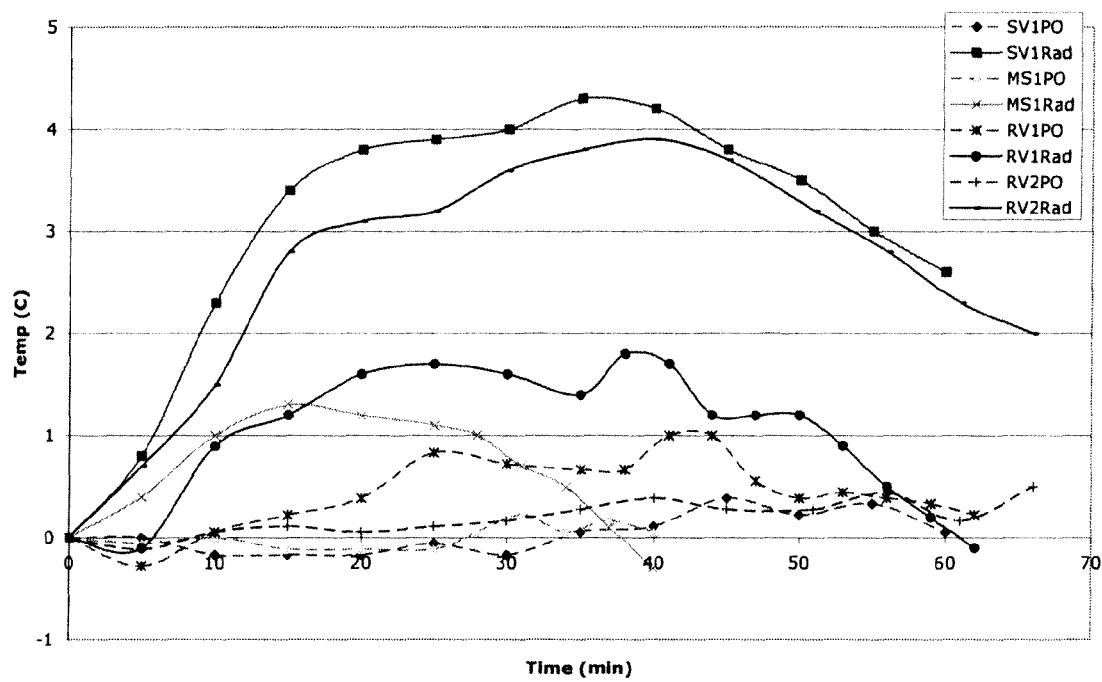
FIG. 7 depicts body temperature measurements using both an oral thermometer and a disclosed device on subjects during exercise.

FIG. 7 indicates change in core body temperature as measured by the radiometer device as compared to oral temperature for subjects. Correlation between the PO and radiometer temperatures were poor in part due to the difficulty in consistently positioning the thermometer as well as the inherent imprecision of thermistor temperature measurements in a dynamic environment. Average correlation coefficient of 0.11+/−0.25. Average R-Square 0.2+/−0.13.

Example 2

This study was designed to compare use of a radiometer device during exercise with measurement of heart rate using a heart rate monitor (HR).

Four runners (MS2, I1, RV3, GS1) were asked to wear a chest-strap type heart rate monitor (Timex) and the radiometer antenna on their chests. They were asked to reach a target heart rate running on a treadmill which they could sustain for 30 minutes as constantly as possible. A reader would record and announce the heart rate on request and the radiometer temperature.

The microwave radiometer was calibrated against fixed temperature water baths at 30 and 40° C. A radiometer antenna was affixed to the chest of the subjects using a large neoprene strap just underneath the left nipple. A cord connected the antenna to the electronics and the data logging PC.

Figure 8:
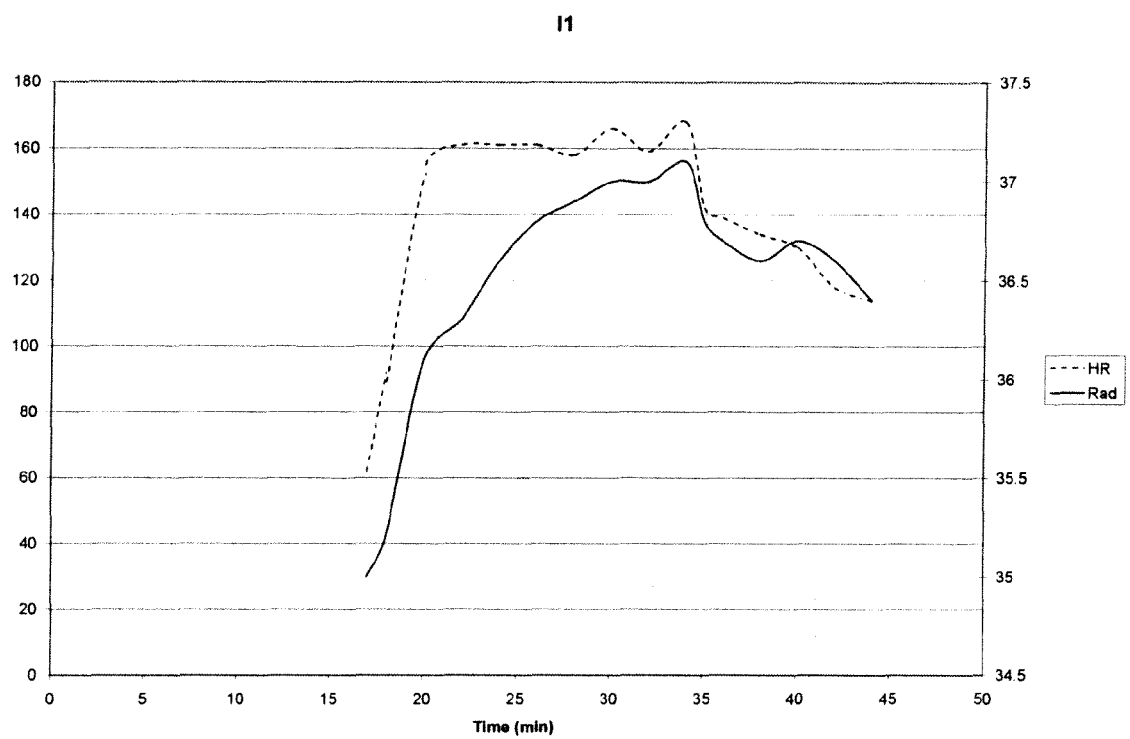
FIG. 8 depicts body temperature measurements and heart rate measurements on a subject during exercise.

Three runners ran for 30 minutes and one runner ran for 19 minutes. Average HR above baseline during run was 92±2 beats per minute. Peak radiometer temperatures were achieved at an average 26±3 minutes. Peak rise in temperature above baseline was 3.5±0.7° C. FIG. 8 compares heart rate to core temperature for subject I1.

REFERENCES

All publications and patents mentioned herein, including those items listed below, are hereby incorporated by reference in their entirety as if each individual publication are patent was specifically and individually incorporated by reference. In case of conflict, the present application, including any definitions herein, will control.

EQUIVALENTS

It is understood that the disclosed disclosure is not limited to the particular methods and devices described as these may vary. It is also to be understood that the terminology used herein is for the purpose of describing particular embodiments only, and is not intended to limit the scope of the present disclosure which will be limited only by the appended claims.

What is claimed is:

1. A method of substantially continuously self-monitoring core body temperature in a subject comprising:

providing a first wearable device to said subject, wherein said first wearable device comprises a transducer for detecting body core microwave emissions indicative of the core body temperature of the subject, a microwave radiometer integrated circuit chip, and a wireless transmission module;

providing a second wearable device suitable for self-monitoring to said subject, wherein said second wearable device comprises a wireless transmission module, a microcontroller, and a display user interface for providing the core body temperature information to said subject;

detecting body core microwave emissions from the subject using the first wearable device;

transmitting said microwave emissions from the first wearable device to the second wearable device; and displaying the core body temperature.

2. The method of claim 1, wherein the subject is exercising.

3. The method of claim 1, wherein the first wearable device includes chest strap.

4. The method of claim 1, wherein the second wearable device includes an article for attaching to a wrist, arm finger, leg, toe or foot of the subject.

* * * * *